United States Patent

Czako et al.

[11] Patent Number: 5,565,685
[45] Date of Patent: Oct. 15, 1996

[54] DUAL INTENSITY ULTRAVIOLET LAMP

[75] Inventors: Eugene Czako, North Haven, Conn.;
Edward A. Stokes, Woodstock, Ill.

[73] Assignee: Light Sources, Inc., Milford, Conn.

[21] Appl. No.: 505,057

[22] Filed: Jul. 21, 1995

[51] Int. Cl.$^6$ .......................................... A61N 5/06
[52] U.S. Cl. .................... 250/504 R; 250/494.1; 607/94; 313/487; 313/488
[58] Field of Search .................. 250/504 R, 494.1, 250/493.1; 607/94; 313/487, 488

[56] References Cited

U.S. PATENT DOCUMENTS

| | | | |
|---|---|---|---|
| 750,554 | 1/1904 | Potter. | |
| 1,792,347 | 2/1931 | Zecher. | |
| 2,916,645 | 12/1959 | Lemmers et al. | 313/493 |
| 3,767,956 | 11/1973 | Bauer | 313/109 |
| 4,194,125 | 3/1980 | Wolff | 250/504 |
| 4,591,958 | 5/1986 | Lamboo | 250/504 R |
| 4,652,790 | 3/1987 | Wood | 313/112 |
| 4,703,184 | 10/1987 | Wolff | 250/504 R |
| 4,959,551 | 9/1990 | Schlitt | 250/504 R |
| 4,967,090 | 10/1990 | Schlitt | 250/504 R |
| 5,008,789 | 4/1991 | Arai et al. | 362/255 |

*Primary Examiner*—Jack I. Berman
*Attorney, Agent, or Firm*—Pepe & Hazard

[57] ABSTRACT

A fluorescent lamp having multiple discrete zones with different levels of radiation intensity along its length has a tube with a fluorescent coating on the interior of the tube adapted to produce ultraviolet radiation of substantially uniform intensity. A reflective coating is provided along a finite length of the tube adjacent one end thereof and about only a portion of the circumference thereof to provide an increased intensity of radiation emanating from the uncoated portion of the periphery of the lamp in the finite portion due to reflection of radiation from the reflective coating. This lamp is especially useful in an array for a tanning chamber to provide a higher intensity of ultraviolet radiation in the facial area.

13 Claims, 2 Drawing Sheets

5,565,685

1

DUAL INTENSITY ULTRAVIOLET LAMP

BACKGROUND OF THE INVENTION

The present invention relates generally to fluorescent lamps, and more particularly to ultraviolet fluorescent lamps providing a higher intensity of ultraviolet radiation adjacent one end.

Tanning salons are becoming very popular, and tanning lamps are also purchased for home and club use. Many devices have been developed to make tanning with the use of artificial illumination sources more enjoyable and efficient. Generally, tanning salons use a booth, chamber, or bed, in or on which a person is placed for exposure to ultraviolet tanning radiation from a number of lamps. Generally, the tanning bed or chamber has a multiplicity of fluorescent lamps that extend longitudinally along the length of the individual and disposed in a parallel array of a width which will uniformly expose the full width of the body. Typically, these lamps are approximately six feet long, or the height of an individual.

Heretofore, these ultraviolet tanning fluorescent lamps have been uniformly coated with a fluorescent coating to provide a uniform radiation intensity over the length, and as many as thirty-six lamps may be used in a single bed or chamber.

It has been recognized that, in most individuals, the face may require a greater amount of ultraviolet radiation than the body in order to obtain the desired uniform tanning effect because of higher levels of melanin in the skin due to more exposure to the sun. To remedy this, some tanning beds or chambers also use metal halide lamps in the area of the head to provide increased radiation to the facial area. Still others interpose relatively short lamps between the longer lamps to provide the desired additional intensity of radiation in the facial area. In this way, the overall duration of time spent in the tanning bed or chamber is held constant while the ultraviolet radiation is increased in intensity in the facial area of the individual to provide the desired uniform tanning over the entire body. Although these composite tanning beds or chambers provide the desired uniform tanning effect, they are more complicated to fabricate and maintain, and they are relatively expensive.

It is an object of the present invention to provide a novel ultraviolet lamp that has a portion adjacent one end thereof providing ultraviolet rays of higher intensity than over the remainder of the lamp.

It is also an object to provide such a lamp which may be fabricated relatively easily and economically, and which will exhibit a relatively long life.

Another object is to provide a tanning bed or chamber which is of relatively simple construction using only these novel lamps so that it can be easily and inexpensively manufactured and maintained, while providing the desired tanning effect by generating increased radiation intensity over the facial area of the individual.

SUMMARY OF THE INVENTION

It has now been found that the foregoing related objects may be readily attained in a fluorescent lamp having discrete multiple zones with different levels of radiation intensity along its length comprising a tube and having a fluorescent coating on the interior of the tube adapted to produce ultraviolet radiation of substantially uniform intensity. A reflective coating is provided on the tube along a finite length adjacent one end thereof and about only a portion of the circumference thereof to provide an increased intensity of radiation emanating from the uncoated portion of the periphery of the lamp in the finite portion.

Preferably, the intensity of radiation emanating in the finite length is between ten to fifty percent greater than the intensity of radiation in the remainder of the lamp, and the finite length is about 8–18 inches so as to provide a sufficient length of enhanced UV radiation over the facial area.

The reflective coating may be provided metallic oxide particles, and the preferred coating is provided by aluminum oxide in a binder. A fluorescent tanning lamp assembly providing a tanning chamber comprises an array of a multiplicity of parallel spaced elongated lamps which embody the present invention.

DETAILED DESCRIPTION OF THE PREFERRED EMBODIMENT

Figure 1:
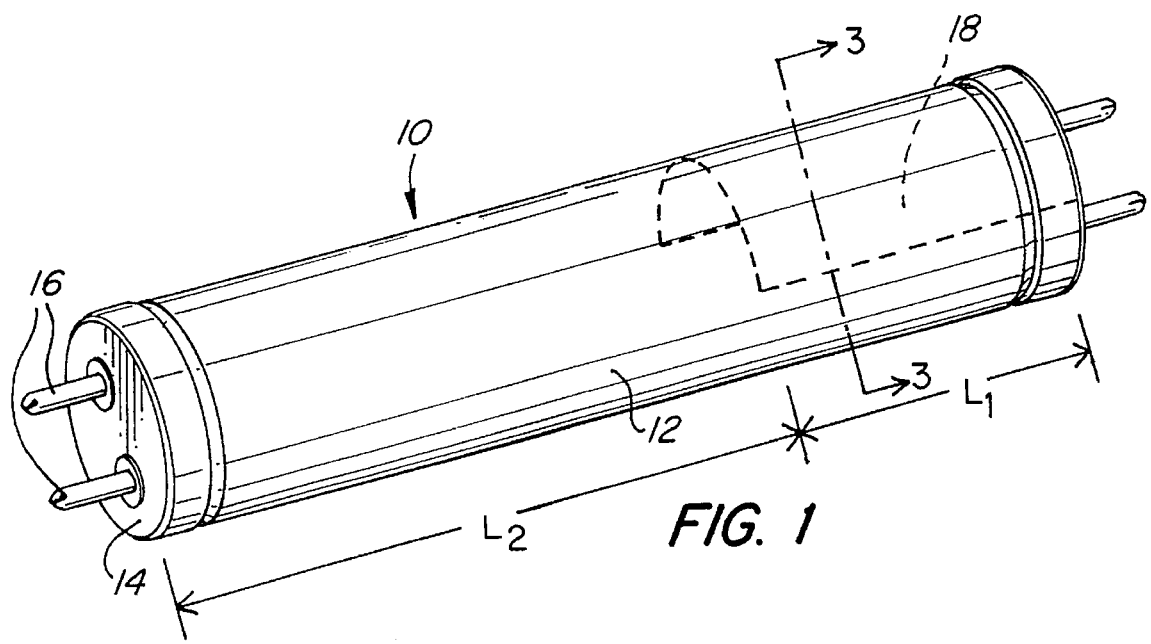
FIG. 1 is a perspective view of a fluorescent lamp embodying the present invention.
Figure 2:
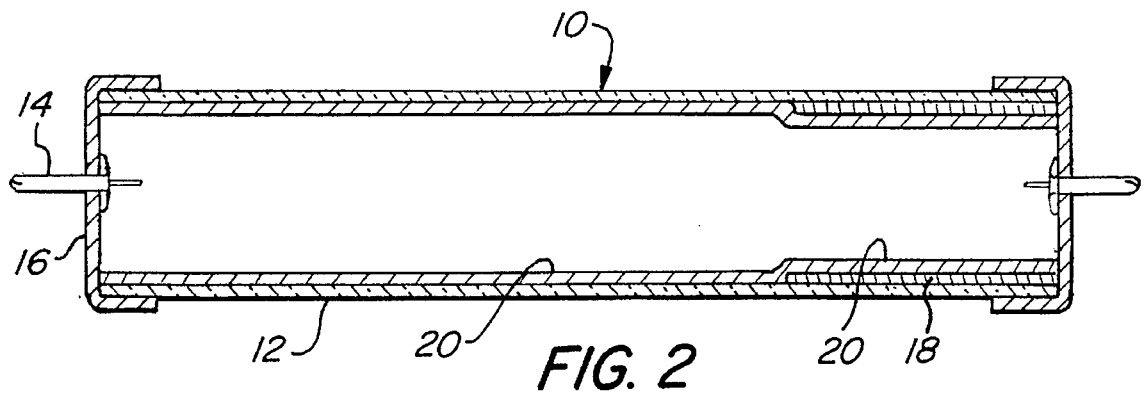
FIG. 2 is a longitudinal cross section taken along the line 2—2 of FIG. 1.
Figure 3:
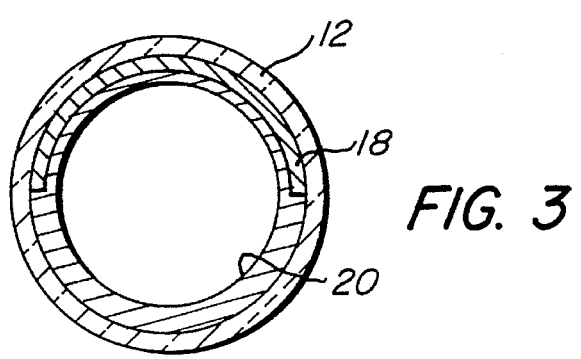
FIG. 3 is a sectional view along the ling 3—3 of FIG. 1.

FIGS. 1 and 2 generally illustrate an ultraviolet fluorescent lamp 10 embodying the present invention and including an elongated tubular glass envelope or tube with end caps 14 at each end. Electrode pins or contacts 16 extend through the caps 14. On the inner surface of the tube 12 adjacent one end is a reflective coating 18 which extends for an axial distance $L_1$ of about 8–18 inches and about 40–60 percent of the periphery of the tube. Extending over the reflective coating 18 and over the remainder $L_2$ of the surface of the tube 12 is a coating 20 of an ultraviolet fluorescing material.

As will be readily appreciated, the reflective coating 18 will reflect ultraviolet radiation from the surface which it covers so that the radiation exiting the tube in the peripheral portion 22 of the length $L_1$ which does not have the reflective coating will be of an intensity which is higher than that emanating over the remainder $L_2$ of the axial length of the tube 12 in which the radiation exits about the entire periphery of the tube 12. Generally, the concentration in the zone $L_1$ will provide an increase in radiation intensity of 10–50 percent.

The reflective coating 18 is produced in accordance with the reflective coating technology presently used to provide such coatings over the full length of the tube, but limiting the application to the relatively short axial length $L_1$. Such reflective coatings frequently utilize a metallic oxide such as aluminum oxide in an organic binder which is typically removed during the subsequent manufacturing process. The reflective coating may also be produced by other deposition techniques such as vapor deposition (PVD, CVD and LECVD) of aluminum or other metals, and by electroless plating. The coating may be on the inside or outside surface of the tube. The reflective coating 18 is applied to the tube prior to application of the fluorescent coating 20, and should cover an arc of about 150°–210°.

The fluorescent coating 20 is produced with the desired ultraviolet intensity or tanning strength and UVB/UVA ratio by known technology. Conveniently, a desired ratio of UVB and UVA radiation of a desired intensity is obtained by mixing known fluorescent materials generating different radiation intensities and spectral ranges. Phillips U-214 sold by Phillips-Elmet of Lewiston, Me. is a well known fluorescent coating material for producing UV radiation as is Nichia NP 806 sold by Nichia America Corporation of Lancaster, Pa. These two well known UV producing fluorescent materials may be mixed in different proportions to produce the desired UV radiation ratio and intensity, and therefore predetermined tanning strengths.

As a specific example, these two UV fluorescent coating materials can be mixed in a ratio of 93:5 to provide a fluorescent coating generating radiation with a UVB/UVA ratio of 0.525 and radiation levels of 2.1 (UVA) and 1.2 (UVB) microwatts/cm$^2$. To provide visible coloration of the radiation, this coating material may also contain 2% by weight of a red fluorescing material such as NP 340 sold by Nichia America.

Figure 5:
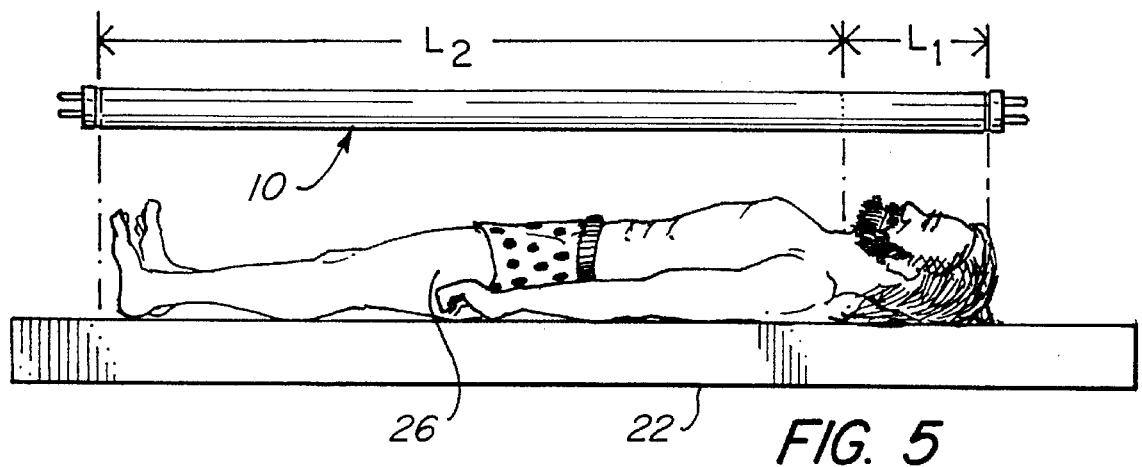
FIG. 5 is a side view of an individual in a tanning chamber employing the lamps of the present invention.

As seen in FIG. 5, the portion of the lamp 10 with the reflective coating 18 is positioned over the facial area of an individual 26 in a tanning chamber 22 so that the desired increased radiation intensity is provided over the head and neck of the individual to produce the desired tanning effect.

As is conventional in tanning chambers and as indicated in FIG. 5, an array of the lamps 10 generally extends longitudinally along the length of the individual. Since the distance $L_1$ for the high intensity radiation is between approximately 12 and 18 inches, or approximately 30 to 46 cm, the distance $L_2$ is 54–60 inches or approximately 137–152 /cm in a six foot (or 1.83 meter) lamp.

The wavelength of the ultraviolet radiation produced by the fluorescent tanning lamp 10 is preferably in a range in the middle ultraviolet region, i.e., 26–380 nanometers.

Although the portion of the lamp having the higher intensity radiation is normally positioned over the face portion of an individual, it may be positioned over any other area of the body.

Figure 4:
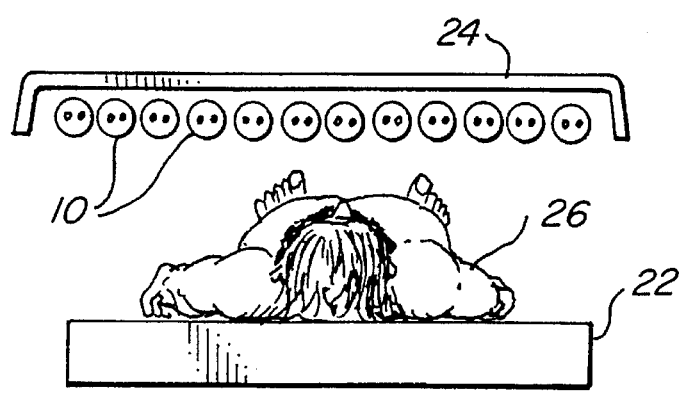
FIG. 4 is a fragmentary end view of a tanning chamber having an array of lamps embodying the present invention as employed.

As seen in FIG. 4, a multiplicity of parallel extending lamps 10 (generally 15–36) is used to provide an array of a width sufficient to provide a uniform intensity across the width of the person 26 in the tanning chamber 22, and generally they are closely spaced.

As seen in FIG. 5, an individual 26 is lying in a tanning chamber 22. The fluorescent lamps 10 of the array are positioned over the individual 26 so that the ultraviolet radiation produced by the fluorescent coating 20 in the zone $L_1$ covers the head and neck of the individual while the lower intensity ultraviolet radiation produced by the fluorescent coating 20 in the zone $L_2$ extends from the neck to the feet. This produces the desired tanning effect in the facial area which will normally require radiation of greater intensity because of the higher melanin level in the skin.

Thus, it can be seen from the foregoing detailed description and attached drawings that the ultraviolet lamp of the present invention produces controlled radiation of different intensity along its axial length. The radiation may also be provided with differentially visible coloration if so desired. The lamps may be fabricated readily and relatively economically and will exhibit relative long life. An array of the novel lamps provides a tanning chamber in which the head region may be exposed to higher intensity radiation than the remainder of the body to provide a uniform tanning effect.

Having thus described the invention, what is claimed is:

1. A fluorescent lamp having multiple discrete zones with different levels of radiation intensity along its length comprising:
    (a) a tube;
    (b) a fluorescent coating on the interior of said tube adapted to produce ultraviolet radiation of substantially uniform intensity; and
    (c) a reflective coating along a finite length of said tube adjacent one end thereof and about only a portion of the circumference thereof to provide an increased intensity of radiation emanating from the uncoated portion of the periphery of said lamp in said finite portion.

2. The fluorescent lamp in accordance with claim 1 wherein the intensity of radiation emanating in said finite length is ten to fifty percent greater than the intensity of radiation in the remainder of the length of said lamp.

3. The fluorescent lamp in accordance with claim 1 wherein said finite length is about 8–18 inches.

4. The fluorescent lamp in accordance with claim 1 wherein such reflective coating includes metallic oxide particles.

5. The fluorescent lamp in accordance with claim 4 wherein said metallic oxide is aluminum oxide and said coating includes a binder as applied.

6. The fluorescent lamp in accordance with claim 1 wherein said portion of said circumference is an arc of 150°–210°.

7. A fluorescent tanning lamp having multiple discrete zones with different levels of radiation intensity along its length comprising:
    (a) a tube;
    (b) a fluorescent coating on the interior of said tube for producing ultraviolet radiation of substantially uniform intensity along the length thereof; and
    (c) a reflective coating along a finite length of about 8–18 inches of said tube adjacent one end thereof and about only a portion of the circumference thereof comprising an arc of 150°–210° to provide an increased intensity of radiation emanating from the uncoated portion of the periphery of said lamp in said finite length, the intensity of radiation emanating in said finite length is ten to fifty percent greater than the intensity of radiation in the remainder of said lamp.

8. The fluorescent tanning lamp in accordance with claim 7 wherein such reflective coating comprises a deposit of aluminum oxide particles in a binder.

9. A fluorescent tanning lamp assembly for a tanning chamber comprising an array of a multiplicity of parallel spaced elongated lamps having multiple discrete zones with different levels of radiation intensity along their length and each comprising:
    (a) a tube;
    (b) a fluorescent coating on the interior of said tube adapted to produce ultraviolet radiation of substantially uniform intensity; and
    (c) a reflective coating along a finite length of about 8–18 inches of said tube adjacent one end of said array and about only a portion of the circumference thereof to provide an increased intensity of radiation emanating from the uncoated portion of the periphery of said lamp in said finite length.

10. The fluorescent tanning lamp assembly in accordance with claim 9 wherein the intensity of radiation emanating in said finite length is ten to fifty percent greater than the intensity of radiation in the remainder of the length of said lamp.

11. The fluorescent tanning lamp assembly in accordance with 9 wherein said finite length is about 8–18 inches.

12. The fluorescent tanning lamp assembly in accordance with 9 wherein such reflective coating includes metallic oxide particles.

13. The fluorescent tanning lamp assembly in accordance with claim 11 wherein said metallic oxide is aluminum oxide and said coating as applied includes a binder.

* * * * *